United States Patent [19]
Bortinger

[11] Patent Number: 5,885,919
[45] Date of Patent: Mar. 23, 1999

[54] PHOSPHORUS/VANADIUM CATALYST PREPARATION

[75] Inventor: Arie Bortinger, Ridgewood, N.J.

[73] Assignee: Scientific Design Company, Inc., Little Ferry, N.J.

[21] Appl. No.: 108,223

[22] Filed: Jul. 1, 1998

Related U.S. Application Data

[63] Continuation-in-part of Ser. No. 903,163, Jul. 30, 1997, abandoned.

[51] Int. Cl.$^6$ ............................ B01J 27/198; B01J 27/14
[52] U.S. Cl. .............................................. 502/209; 502/208
[58] Field of Search ...................................... 502/208, 209

[56] References Cited

U.S. PATENT DOCUMENTS

| | | | |
|---|---|---|---|
| 4,116,868 | 9/1978 | Mount et al. | 502/209 |
| 4,149,992 | 4/1979 | Mount et al. | 502/209 |
| 4,454,342 | 6/1984 | Gaffney et al. | 502/209 |

*Primary Examiner*—Elizabeth Wood
*Attorney, Agent, or Firm*—William C. Long

[57] ABSTRACT

The invention provides an improved method for the production of vanadium/phosphorous mixed oxide catalysts, using an organic solvent system and an additive such as dimethyl sulfoxide, the catalyst having special utility in the production of maleic anhydride.

6 Claims, 2 Drawing Sheets

PHOSPHORUS/VANADIUM CATALYST PREPARATION

RELATED APPLICATION

This application is a continuation-in-part of application Ser. No. 08/903,163 filed Jul. 30, 1997 and now abandoned.

BACKGROUND OF THE INVENTION

1. Field of the Invention

The present invention relates to an improved method for the preparation of vanadium/phosphorus mixed oxide catalysts, using an additive such as dimethyl sulfoxide during the preparation, the catalyst having special utility in the production of maleic anhydride.

2. Description of the Prior Art

Catalysts containing vanadium and phosphorus oxides have been used in the oxidation of 4-carbon atom hydrocarbons, such as n-butane, with molecular oxygen or oxygen containing gas to produce maleic anhydride. Conventional methods of preparing these catalysts involve reducing a pentavalent vanadium compound, and if desired, promoter element compounds under conditions which will provide or maintain vanadium in a valence state below +5 to form catalyst precursors which are recovered and calcined.

Hydrogen chloride has been used as a reducing agent for vanadium compounds where vanadium has a +5 valence. The use of gaseous HCl as a reducing agent is disclosed in U.S. Pat. No. 4,002,650 where the vanadium and phosphorus components are reacted in an aqueous solution. The use of gaseous HCl as a reducing agent for vanadium compounds such as $V_2O_5$ is also described in U.S. Pat. No. 4,043,943 where the vanadium and phosphorus components are reacted in liquid organic medium.

U.S. Pat. No. 5,137,860 provides a comprehensive description of the prior art in this area. The patent shows the use of organic reducing agents as well as hydrogen chloride and teaches the use of activation procedures whereby the catalyst precursor is contacted at prescribed conditions with oxygen and steam mixtures and finally with a non-oxidizing steam atmosphere to produce an active catalyst.

U.S. Pat. No. 4,569,925 describes the preparation of vanadium/phosphorus mixed oxide catalysts by an organic solution method using anhydrous hydrogen chloride as an agent for the solubilization of the vanadium component, and teaches an activation procedure whereby the catalyst precursor is contacted not with air alone but with a mixture of air and a hydrocarbon such as methane, ethane, propane, butane and the like.

U.S. Pat. Nos. 4,116,868 and 4,149,992 describe the preparation of vanadium/phosphorus catalysts wherein a surfactant is employed in the preparation procedure. Among the many surfactants suggested are dialkyl sulfoxides having a $C_{10}$–$C_{18}$ alkyl group.

There are problems associated with the use of hydrogen chloride in the preparation of catalysts. The corrosion problems are obvious. Even after calcination to prepare the catalyst, residual chloride remains in the catalyst. The chloride is generally removed during the catalyst activation period in the reactor or in a separate step outside the reactor, but chloride release from the solid catalyst into the reactor and the downstream equipment in the process is undesirable. The main problems are: possible equipment corrosion, product loss during chloride liberation and increased waste disposal. It would be advantageous to provide a method for the preparation of VPO catalysts wherein the use of chloride materials could be substantially or completely avoided.

The synthesis of VPO catalysts can be carried out both in aqueous and in organic solvent media. Anhydrous conditions are preferred in the organic solvent method. The synthesis in organic solvents is presently the preferred method due to the better performance of the catalyst. This is attributed to greater surface areas of the catalyst when prepared in organic solvent than in aqueous media (G. J. Hutchings, Applied Catalysis, 72(1991), 1–32 and references therein).

In the organic solvent method typically employing isobutanol, anhydrous HCl has been used as reducing agent for the $V_2O_5$. Other reducing agents have been used such as oxalic acid or organic alcohols such as allyl alcohol, benzyl alcohol and isobutanol which can be both the solvent and reducing agent. With HCl, the $V_2O_5$ is converted to an IBA (isobutyl alcohol) soluble material ($VOCl_2$) prior to the addition of phosphoric acid. In the absence of HCl, the $V_2O_5$ is not solubilized and the formation of the VPO catalyst is done heterogeneously on the suspended $V_2O_5$ in the organic solvent. The use of HCl has produced excellent catalysts but the residual chloride in the catalyst results in a chloride release during catalyst activation which is undesirable. This difficulty can be overcome by removing the chlorides through an additional step during the catalyst manufacturing.

Synthesis of VPO catalyst without HCl eliminates the use of this corrosive gas during production, reduces costs associated with waste disposal and eliminates the need to remove the residual chloride from the catalyst.

BRIEF SUMMARY OF THE INVENTION

In accordance with the invention, a mixed vanadium/phosphorus oxide catalyst is prepared in an organic solvent procedure which involves the use of an additive such as dimethyl sulfoxide; especially good results are achieved where a bismuth catalyst promoter is also employed.

DETAILED DESCRIPTION

The present invention provides a method for the preparation of a phosphorus/vanadium/oxygen catalyst which is especially useful in the oxidation of n-butane to maleic anhydride wherein a vanadium compound in the +5 valence state, eg. vanadium pentoxide, is reduced in an organic medium which contains an organic sulfoxide additive which participates in vanadium reduction and is reacted with concentrated phosphoric acid. The invention can be carried out in a single step, thus greatly simplifying catalyst preparation. After formation of the catalyst precursor, the precursor can be converted to the active form in accordance with known procedures.

Organic sulfoxide modifying agents which are employed in the invention have the formula:

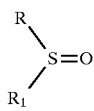

wherein R and R$_1$ are the same or different groups having 1–8 carbon atoms selected from alkyl, substituted alkyl, aryl and substituted aryl groups. Preferred are sulfoxides wherein each of R and R$_1$ are alkyl groups having 1–4 carbon atoms and especially preferred are sulfoxides wherein each of R and R$_1$ is an alkyl group having 1–2 carbon atoms. Dimethyl sulfoxide is preferred, other illustrative sulfoxides are methyl ethyl sulfoxide, diethyl sulfoxide, di-isopropyl sulfoxide, di-n-butyl sulfoxide, and the like.

The role of the organic sulfoxide in the preparation of catalyst and the nature of the mechanism by which catalyst performance is improved are not clearly understood. It is possible that the sulfoxide plays a role in the oxidation/reduction reactions during the catalyst formation. When the product is recovered there is a strong smell of a sulfur compound which is not observed without use of organic sulfoxide and is not present in the initial reaction mixture. Organic sulfoxide can both undergo oxidation to the sulfone, but also possibly can be reduced to the sulfide in our reaction mixture. As discussed later, the sulfur compound odor can be obviated by treatment with an oxidizing agent such as hydrogen peroxide.

It is well known that solvent can have a large effect on catalyst due to intercalation, and it is possible that the sulfoxide has such effect. It is clear that the organic sulfoxide has an effect on the crystallite morphology. This is shown by SEM data; note, FIGS. 1 to 4. Dimethyl sulfoxide is miscible both in organic solvent and in water.

Figure 1:
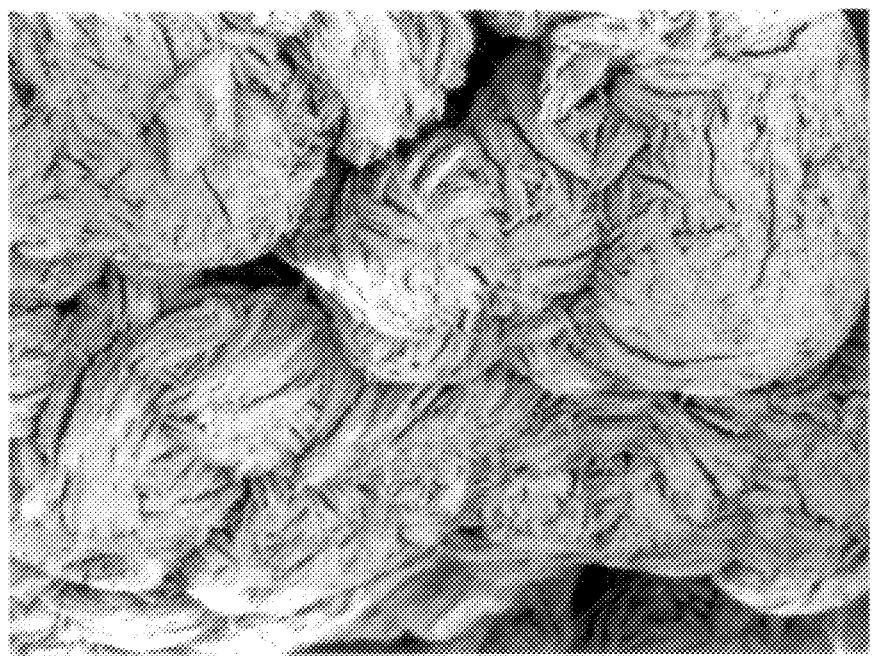
FIG. 1 is a scanning electron micrograph of a catalyst prepared according to the invention.
Figure 2:
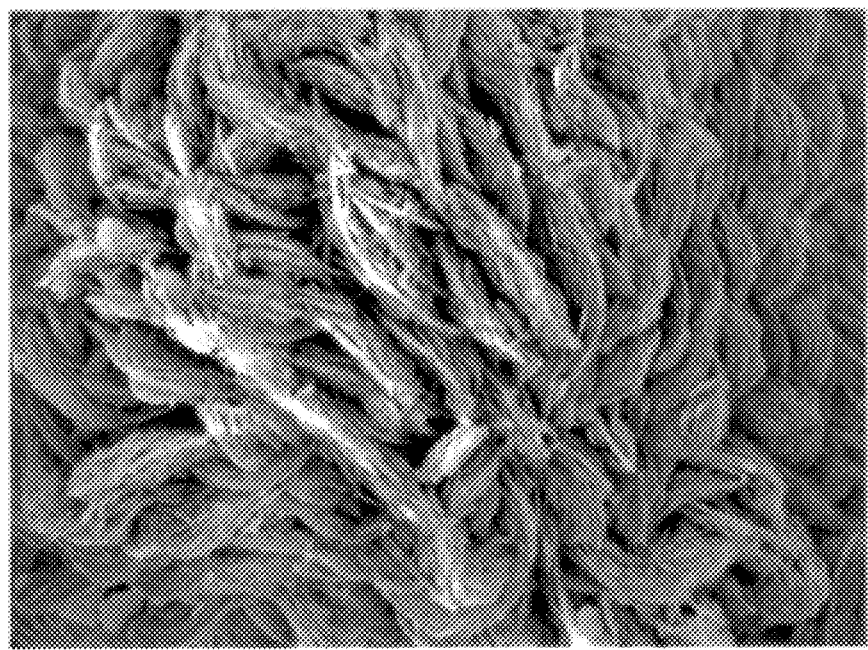
FIG. 2 is a scanning electron micrograph of a catalyst prepared by conventional procedures and presented for comparative purposes.

FIGS. 1 and 2 are scanning electron micrographs at 10,000 times enlargement comparing surface morphology of catalysts prepared by the invention (FIG. 1) with comparable catalyst prepared in accordance with conventional procedures (FIG. 2). Examination of these FIGS. 1 and 2 demonstrates that there is considerably greater spacing between platelet layers of the conventional catalyst and that the preparation procedure of the invention where dimethyl sulfoxide was used resulted in a much denser platelet layer packing and in the formation of spool shaped morphology.

Figure 3:
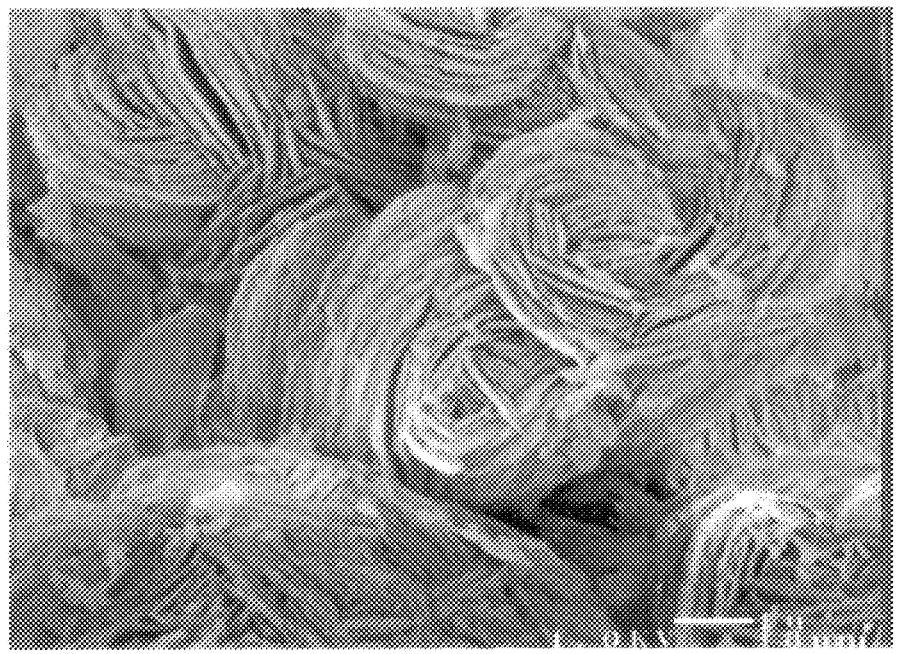
FIG. 3 is a scanning election micrograph of a bismuth promoted catalyst prepared according to the invention.
Figure 4:
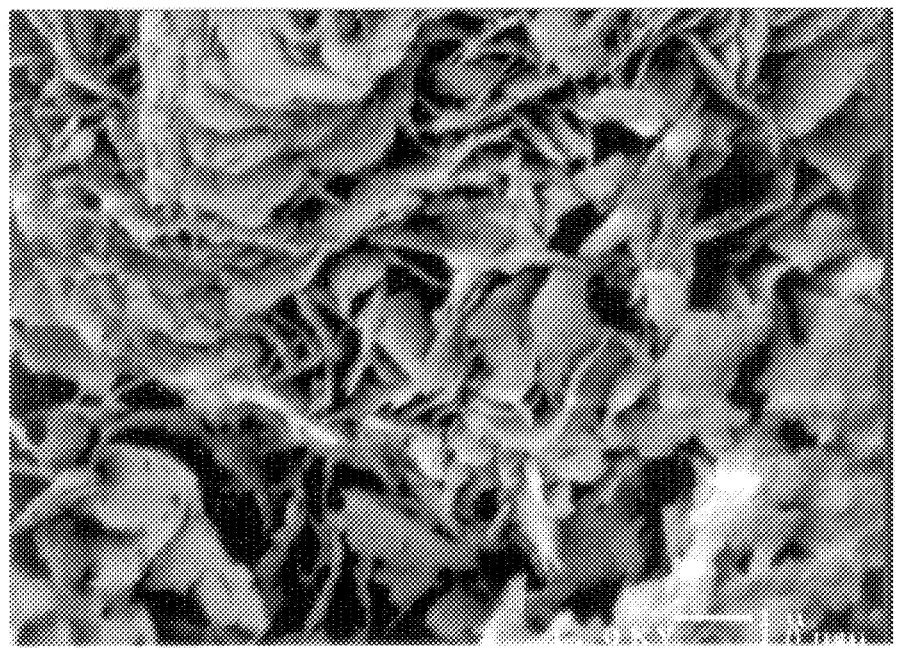
FIG. 4 is a scanning electron micrograph of a bismuth promoted catalyst prepared by conventional procedures and presented for comparative purposes.

FIGS. 3 and 4 present a similar comparison with catalysts comprised of bismuth promoter. The catalyst prepared according to the invention (FIG. 3) also has denser platelet layer packing and spool shaped morphology as compared with a similar catalyst prepared by conventional procedures (FIG. 4).

In carrying out the invention, vanadium pentoxide in finely divided form is added to an organic solvent medium to which is also added an effective amount of the organic sulfoxide reducing agent. Suitable solvents are alcohols known in this art such as, for example, a primary or secondary alcohol including methanol, ethanol, 1-propanol, 2-propanol, butanol, 2-butanol, 2, methyl-1-propanol, 3-methyl-2-butanol, 2, 2-dimethyl-1-propanol, 1-hexanol, 4-methyl-1-pentanol, 1-heptanol, 4-methyl-1-hexanol, 4-methyl-1-heptanol, benzyl alcohol, 1,2-ethanediol, glycerol, trimethylopropane, 4-methyl, 2-pentanone, diethylene glycol and trimethylene glycol or mixtures thereof. The alcohols can also function as reducing agents for the vanadium +5 compound.

Generally, the organic sulfoxide is used in an amount which corresponds to a ratio of mols sulfoxide to atoms of vanadium of 0.001 to 1 and preferably 0.001 to 0.5 mols sulfoxide per atom of vanadium.

It is advantageous to incorporate catalyst promoters or modifiers in the catalyst and compounds of these components can be conveniently added to the organic solvent mixture initially or at a later stage after the catalyst precursor has been formed. Any of the known promoters can be used although it is especially advantageous to use a combination of Zn, Li and Mo promoters which are conveniently added as soluble compounds to the organic solvent. Especially outstanding results are achieved where a bismuth promoter is used. Other promoters include those described in U.S. Pat. Nos. 3,980,585, 4,056,487, 4,515,904, 4,147,661, 4,418,003, and the like the disclosures of which are incorporated herein by references.

In especially preferred practice, concentrated phosphoric acid is also added to the vanadium containing organic solvent solution which also contains the dialkyl sulfoxide and optionally the promoter compound or compounds, and the resulting mixture is digested at about 20° to 200° C. for a period of 1 to 24 hours.

In a less preferred embodiment, the phosphoric acid can be added after the vanadium pentoxide has been reduced in the organic solvent solution and the resulting mixture then digested to form the catalyst precursor.

The reduction and digestion procedures are carried out to form a VPO catalyst complex which is characterized as a mixed oxide; however, the structure of the complex has not been determined but may be conveniently represented by a formula such as VP$_a$Me$_y$O$_x$, 'a' being 0.90 to 1.3. Me is a metal such as Bi, Zn or Mo, an alkali metal or alkaline earth metal as known in the art as modifiers for catalysts of this type. This representation is not an empirical formula and has no significance other than representing the atom ratio of the components of the catalyst. The 'x' and 'y' in fact, have no determinant value and can vary widely depending on the combinations within the complex. That there is oxygen present is known, and the O$_x$ is representative of this.

To obtain the mixed oxides of vanadium and phosphorus, phosphoric acid of approximately 100% H$_3$PO$_4$ (98 to 101%) is added. Superphosphoric acid (105–115%) can also be used while maintaining the desired P/V rate. Digestion of the vanadium compound is discerned by a change in the color of the reaction mixture to a dark blue green, the alcohol can be partially stripped or not and the precursor recovered by filtration and thereafter dried to produce the dried catalyst precursors.

The digestion of the vanadium compound in the phosphoric acid is normally conducted at reflux until the color change indicates transformation to the VPO precursor during the digestion.

The final removal of alcohol and sulfoxide or derivative is carried out in a drying step in an oven at a temperature in the range of 100° to 180° C. for 1–24 hours. Lower temperatures and longer times can be used. Reduced pressure can also be applied during the drying step. Following drying, calcination of the dried catalyst precursor is carried out at a temperature in the range of about 200° to 300° for a sufficient period to improve the catalytic properties of the composition and remove volatile materials, usually 1–15 hours. The catalyst powder after the calcination step or even after the drying step is mixed with a lubricant such as graphite and fabricated to the desired geometric shape.

Following calcination, the catalyst precursor is activated by contact with a gas containing a mixture of Air/N$_2$/steam. This contact takes place at 350°–550° C., for about 1–10 hours and results in the formation of catalyst which can then be used in the production of maleic anhydride.

Preferred catalyst complexes are characterized as a mixed oxide, however, the structure of the complex has not been determined but may be conveniently represented in the case of Zn, Mo and Li promoters by a formula such as $VP_aZn_bMo_cLi_dO_x$ where 'a' is 0.9 to 1.3, 'b' is 0.001 to 0.15, 'c' is 0.005 to 0.10 and 'd' is 0.001 to 0.15. The catalyst can, of course, contain promoters in addition to those indicated in the above formula.

When Zn promoter is used, generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalysts as well as those of the prior art in the mole ratio of P/V 0.9–1.3/1. Optimum P/V ratios are found to be below 1.25/1 and above 1.0/1. Where lithium is used, lithium component is present at an atomic ratio of 0.001 to 0.15/1, Li/V. Where molybdenum is used, the Mo/V atomic ratio is suitably 0.005 to 0.10, Mo/V.

Bismuth promoted catalyst complexes can be characterized by the formula $VP_aBi_eO_x$ where 'a' and 'x' are as above described and 'e' is 0.001 to 0.15, preferably 0.005 to 0.07. The catalyst can, of course, contain promoters in addition to the bismuth.

Bismuth is a preferred promoter and is conveniently used in an atomic ratio of B/V in the range 0.001 to 0.15/1, preferably 0.005 to 0.07/1.

The modifier components are added as the compound thereof such as acetates, acetylacetonates, carbonates, chlorides, bromides, oxides, hydroxides, phosphates and the like, e.g. a bismuth salt of an organic acid or mixture of organic acids such as bismuth ethyl hexanoate, zinc acetyl acetonate, zinc acetate, lithium acetate, lithium carbonate, lithium oxide, or lithium orthophosphate and the like.

The molybdenum compound may be dissolved in an organic solvent, as described above or water and added to the reaction mixture. The solvent containing the molybdenum compound may be added with the other modifiers or at different times. The use of a soluble molybdenum compound dissolved in a solvent according to the present invention for addition to the reaction mixture has been found to be particularly effective in dispersing the molybdenum throughout the mixture and the final dried catalyst. Some examples of suitable soluble molybdenum catalyst include phosphomolybdic acid, ammonium molybdate (VI) tetrahydrate, lithium molybdate, molybdenum tetrabromide, molybdenum trioxyhexachloride and the like.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, and alkene, n-butane, for the production of maleic anhydride, which has a wide commercial usage.

The oxidation of the n-$C_4$ hydrocarbon to maleic anhydride may be accomplished by contacting e.g. n-butane in low concentrations in oxygen with the described catalyst. Air is entirely satisfactory as a source of oxygen, but synthetic mixtures of oxygen and diluent gases, such as nitrogen also may be employed. Air enriched with oxygen may be employed.

The gaseous feed stream to the standard tubular oxidation reactors normally will contain air and about 0.5 to about 3.0 mole percent hydrocarbons such as n-butane. About 1.0 to about 2.5 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole percent can be used without explosive hazard. Lower concentrations of $C_4$, less than about one percent, or course, will reduce the total productivity obtained at equivalent flow rates and thus are not normally economically employed.

The flow rate of the gaseous stream through the reactor may be varied within rather wide limits but a preferred range of operations is at the rate of about 10 to 300 grams of $C_4$ per liter of catalyst per hour and more preferably about 50 to about 250 grams of $C_4$ per liter of catalyst per hour. Residence times of the gas stream will normally be less than about 4 seconds, more preferably less than about one second, and down to a rate where less efficient operations are obtained. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼" to about 3", and the length may be varied from about 3 to about 18 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon steel, nickel, glass tubes have excellent long life under the conditions for the reactions described herein. Normally, the reactors contain a preheat zone of an inert material such as ¼' Alundum pellets, inert ceramic balls, nickel balls or chips and the like, present at about ½ to ¹⁄₁₀ the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 380° C. to about 475° C. Described another way, in terms of salt bath reactors with carbon steel reactor tubes about 1.0" in diameter, the salt bath temperature will usually be controlled between about 350° C. to about 550° C. Under normal conditions, the temperature in the reactor ordinarily should not be allowed to go above about 475° C. for extended lengths of time because of decreased yields and possible deactivation of the catalyst.

The reaction may be conducted at atmospheric, super atmospheric or below atmospheric pressure. The exit pressure will be at least slightly higher than the ambient pressure to insure a positive flow from the reaction. The pressure of the gases must be sufficiently high to overcome the pressure drop through the reactor.

The maleic anhydride may be recovered in a number of ways well known to those skilled in the art. For example, the recovery may be by direct condensation or by absorption in suitable media, with subsequent separation and purification of the maleic anhydride.

EXAMPLE 1

Into a 12 liter round flask equipped with a mechanical stirrer, a gas inlet tube, thermowell, Dean Stark trap with a condenser and a heating mantle were charged 5672 ml anhydrous isobutanol, 1613 ml benzyl alcohol, 35 grams of dimethyl sulfoxide, (DMSO), 815.1 grams $V_2O_5$ of mostly less than 10 micron particle size, 4.57 grams lithium acetate dihydrate, 47.25 grams zinc acetylacetonate hydrate and 22.97 grams of 12-molybdophosphoric acid. About 1098 g of 100% phosphoric acid were added slowly into the reaction mixture while stirring. Another 780 cc of isobutanol was used to rinse the phosphoric acid and promoter containers.

The reaction mixture was brought to reflux which was continued overnight. Thereafter, about 4032 ml distillate were removed and the reaction mixture was cooled down and filtered. The product cake was divided into two parts and each part was washed with about 700–1000 cc of fresh isobutanol. The product was then dried in the oven at 110° C. for 10 hours and finally at 150° C. for 16 hours. The dry cake was then crushed and calcined at 220° C. for 3 hours and then at 260° C. for another 3 hours. The calcined powder was mixed with 4% graphite and was formed into 3/16"×3/16" tablets with a 1/16" I.D hole struck therethrough. The catalyst in the pellet form was than activated in an oven with 3/1 volume mixture of steam/air at about 425° C. for 1 hour followed by 6 hours in which the air was replaced with nitrogen. The catalytic activity is shown in Table 1.

The performance test is done in a 5 foot stainless steel reactor tube, 1 inch O.D. packed with a 3.5 feet catalyst bed. Air in the feed is balanced with the % butane used in the reaction to a total of 100%.

EXAMPLE 2

The synthesis of example 1 was generally repeated except that DMSO/V was increased to 0.1. The catalytic activity is shown in Table 1.

EXAMPLE 3

The synthesis of example 1 was generally repeated except that DMSO/V was increased to 0.2. The catalytic activity is shown in Table 1.

EXAMPLE 4

The synthesis of example 1 was generally repeated except that DMSO/V was increased to 0.35. The catalytic activity is shown in Table 1.

TABLE 1[1]

| Effect of DMSO/V ratio in 20% benzyl alcohol in IBA | | | | |
|---|---|---|---|---|
| EXAMPLE | 1[2] | 2[3] | 3 | 4 |
| DMSO/V | 0.05 | 0.1 | 0.2 | 0.35 |
| HOURS | 1026 | 514 | 940 | 943 |
| SALT °C. | 404 | 401 | 410 | 391 |
| HOT SPOT °C. | 438 | 459 | 446 | 459 |
| % BUTANE | 1.31 | 1.19 | 1.29 | 1.29 |
| % CONVERSION | 78.9 | 79.2 | 79.7 | 79.5 |
| % SELECTIVITY | 69.9 | 71.0 | 66.0 | 65.5 |
| Wt % YIELD | 93.4 | 95.0 | 88.9 | 88.1 |

[1]1" × 5' Reactor; 3.5' bed with thermowell; 3/16" × 3/16" with 1/16" hole in center. The space velocity in examples 1–4 was 2500h$^{-1}$
[2]0.8 ppm trimethyphosphite was added into the feed
[3]0.3 ppm trimethyphosphite was added into the feed The experimental results shown in Table 1 demonstrate the higher selectivities and yields at dimethyl sulfoxide/V ratios below 0.2.

EXAMPLE 5 (COMPARATIVE)

The synthesis of example 1 was generally repeated except that DMSO/V was 0 and the lithium acetate salt was increased to 9.14 grams. The catalytic activity is shown in Table 2.

EXAMPLE 6

The synthesis of example 5 was generally repeated except that the dimethyl sulfoxide reducing agent was used; the DMSO/V ratio was 0.1. The catalytic activity is shown in Table 2.

EXAMPLE 7

The catalyst was prepared as shown in example 6 except that the steam:air was changed to 1:1 during activation. The catalytic activity is shown in Table 2.

TABLE 2[1]

| Performance of Catalyst Prepared With & Without DMSO | | | |
|---|---|---|---|
| EXAMPLE | 5[2] | 6 | 7 |
| DMSO/V | 0 | 0.1 | 0.1 |
| HOURS | 992 | 1001 | 1109 |
| SALT °C. | 406 | 405 | 408 |
| HOT SPOT °C. | 465 | 453 | 455 |
| % BUTANE | 1.22 | 1.21 | 1.30 |
| % CONVERSION | 80.3 | 80.2 | 80.0 |
| % SELECTIVITY | 69.0 | 69.8 | 69.3 |
| Wt % YIELD | 93.6 | 94.6 | 93.5 |

[1]1" × 5' Reactor; 3.5' bed with thermowell; 3/16" × 3/16" with 1/16" hole in center. The space velocity in examples 5–7 was 2500h$^{-1}$
[2]comparative From the data given above, it can be seen that the catalysts prepared in accordance with the invention have a lower hot spot as well as improved selectivity and yield after extended use when compared to a catalyst prepared without the use of the dimethyl sulfoxide.

EXAMPLE 8

This catalyst was prepared as shown in example 7 except that the reflux step was reduced to 4 hours time and the drying step was done under vacuum. The catalyst was activated as in example 7. The catalytic activity is shown in Table 3.

EXAMPLE 9

This catalyst was prepared as shown in example 7 except that the drying step was done under vacuum and the catalyst was pelletized without a calcination step. The catalyst was activated as in example 7 except that it was first held at 200° C. under nitrogen for 90 minutes. The catalytic activity is shown in Table 3.

TABLE 3[(1)]

| Performance of Catalyst Prepared With DMSO | | |
|---|---|---|
| EXAMPLE | 8 | 9 |
| HOURS | 221 | 215 |
| SALT °C. | 396 | 396 |
| HOT SPOT °C. | 456 | 442 |
| % BUTANE | 1.20 | 1.20 |
| % CONVERSION | 79.4 | 78.2 |
| % SELECTIVITY | 71.0 | 72.4 |
| Wt % YIELD | 95.2 | 95.6 |

[(1)]1" × 5' Reactor; 3.5' bed with thermowell; 3/16" × 3/16" with 1/16" hole in center. The space velocity in examples 8–9 was 2500h$^{-1}$.

The data shown above demonstrates the excellent results obtained with catalysts prepared using the dimethyl sulfoxide additive according to the invention and using somewhat different preparation procedures.

For comparative purposes, catalysts were prepared in accordance with procedures shown in various references.

COMPARATIVE EXAMPLE A

The purpose of the comparative example is for the comparison of the wet end synthesis step. The procedures of example 7 (catalyst #12) of U.S. Pat. No. 5,364,824 were repeated. The catalyst shape was as in example 1. The catalyst was activated as in example 7. The catalytic activity is shown in Table 4.

COMPARATIVE EXAMPLE B

The purpose of the comparative example is for the comparison of the wet end synthesis step. The procedure of example 12 of U.S. Pat. No. 5,506,187 were repeated except that the catalyst shape was as in example 1. The catalytic activity is shown in Table 4.

COMPARATIVE EXAMPLE C

The purpose of the comparative example is to show the effect of using oxalic acid in the presence of Mo instead of DMSO.

Into a 12 liter round flask equipped with a mechanical stirrer, a gas inlet tube, thermowell, Dean Stark trap with a condenser and a heating mantle were charged 5672 ml anhydrous isobutanol, 1613 ml benzyl alcohol, 363.2 grams of oxalic acid, 815.1 grams $V_2O_5$ of mostly less than 10 micron particle size, 9.14 grams lithium acetate dihydrate, 47.25 grams zinc acetylacetonate hydrate and 22.97 grams of 12-molybdophosphoric acid. About 1098 g of 100% phosphoric acid were added slowly while stirring into the reaction mixture. Another 780 cc of IBA was used to rinse the phosphoric acid and promoters containers.

The reaction mixture was brought to reflux which was continued overnight. Thereafter, about 4032 ml distillate were removed and the reaction mixture was cooled down and filtered. The product cake was divided into 2 and each part was washed with about 700–1000 cc of fresh IBA. The product was then dried in the oven at 110° C. for 10 hours and finally at 150° C. for 16 hours. The dry cake was then crushed and calcined at 220° C. for 3 hours and then at 260° C. for another 3 hours. The calcined powder was mixed with 4% graphite and was formed into 3/16"×3/16" tablets with a 1/16" I.D hole struck therethrough. The catalyst in the pellet form was than activated in an oven with 3/1 volume ration of steam/air at about 425° C. for 1 hour followed by 6 hours in which the air was replaced with nitrogen. The catalytic activity is shown in Table 4.

TABLE 4[(1)]

| Performance of Comparative Catalysts | | | |
|---|---|---|---|
| COMPARATIVE EXAMPLE | A | B | C |
| HOURS | 1121 | 988 | 530 |
| SALT °C. | 403 | 387 | 424 |
| HOT SPOT °C. | 450 | 422 | 464 |
| % BUTANE | 1.31 | 1.20 | 1.11 |
| % CONVERSION | 80.0 | 80.9 | 79.6 |
| % SELECTIVITY | 66.7 | 62.0 | 68.8 |
| Wt % YIELD | 90.3 | 84.8 | 92.4 |

[(1)]1" × 5' Reactor; 3.5' bed with thermowell; 3/16" × 3/16" with 1/16" hole in center. The space velocity in examples A–B was 2500h$^{-1}$ and only 2000h$^{-1}$ in example C.

EXAMPLE 10

Into a 12 liter round flask equipped with a mechanical stirrer, a gas inlet tube, thermowell, Dean Stark trap with a condenser and a heating matle were charged 6452 ml anhydrous isobutanol, 1613 ml benzyl alcohol, 70 grams of DMSO (Dimethyl sulfoxide), 815.1 grams $V_2O_5$, 66.9 grams of 28% Bi Hex-Cem (this is a Bi salt of 2 ethyl hexanoic acid in a mineral spirits carrier). About 1098 g of 100% phosphoric acid were added slowly into the reaction mixture while stirring. The particle size of the $V_2O_5$ used was mainly greater than 150 microns.

The reaction mixture was brought to reflux which was continued overnight. Thereafter, about 4032 ml distillate were removed and the reaction mixture was cooled down and filtered. The product cake was divided in two and each part was washed with about 700–1000 cc of fresh IBA. The product was then dried in an oven at 110° C. for 10 hours and finally at 150° C. for 16 hours. The dry cake was then crushed and calcined at 220° C. for 3 hours and then at 260° C. for another 3 hours. The calcined powder was mixed with 4% graphite and was formed into 3/16"×3/16" tablets with a 1/16" I.D. hole struck there through. The catalyst in the pellet form was than activated in an oven with 50% steam/50% air at about 425° C. for 1 hour followed by 6 hours in which the air was replaced with nitrogen. The catalytic activity is shown in Table 5.

The performance test is done in a 5 foot stainless steel reactor tube, 1 inch O.D. packed with a 3.5 feet catalyst bed. Air in the feed is balanced with the % butane used in the reaction to a total of 100%.

EXAMPLE 11

The synthesis of example 10 was generally repeated except that no DMSO was present. The catalytic activity is shown in Table 5.

EXAMPLE 12

The synthesis of example 10 was generally repeated except that the distillation step was eliminated. The catalytic activity is shown in Table 5.

EXAMPLE 13

The synthesis of example 12 was generally repeated except that the filtered cake was not rinsed as described in example 10. The catalytic activity is shown in Table 5.

EXAMPLE 14

The synthesis of example 12 was generally repeated except that after the reaction mixture was cooled down, 80 ml of 30% hydrogen peroxide were added while stirring. After about 30 minutes of stirring, the reaction mixture was filtered and the remaining procedures of Example 13 were followed. The catalytic activity is shown in Table 6.

As a result of the hydrogen peroxide addition, sulfur compound odor, normally associated with the product, was eliminated. In place of hydrogen peroxide, other peroxidic oxidizing agent can be used to obviate sulfur compound odor including hydroperoxides, peroxides and the like as illustrated by t-butyl hydroperoxide, t-butyl peroxide, benzyl peroxide, and the like.

EXAMPLE 15

The synthesis of example 13 was generally repeated except that the amount of benzyl alcohol was reduced by half while maintaining the total volume of alcohols the same. The catalytic activity is shown in Table 6.

EXAMPLE 16

A large composite of catalyst prepared as shown in Example 10 was tested in a commercial size reactor 1"×12 ft. with a catalyst bed height of 10.5 ft. Test results are shown in Table 7.

COMPARATIVE EXAMPLE D

The purpose of the comparative example is for the comparison of the wet end synthesis step. The procedures of example 7 (catalyst #12) of U.S. Pat. No. 5,364,824 were repeated. The vanadium pentoxide particle size used was mostly greater that 150 microns. The catalyst shape was as in example 10. The catalyst was activated as in example 10 and tested in a commercial size reactor as in Example 18. The catalytic activity is shown in Table 7.

TABLE 5[1]

| Example      | 10   |      | 11[2] |      | 12   |      | 13   |      |
|--------------|------|------|-------|------|------|------|------|------|
| Hours        | 361  | 998  | 349   | 483  | 355  | 658  | 349  | 935  |
| Salt °C.     | 384  | 381  | 388   | 389  | 394  | 395  | 383  | 382  |
| Hot Spot °C. | 433  | 440  | 445   | 452  | 446  | 450  | 430  | 435  |
| % Butane     | 1.31 | 1.30 | 1.26  | 1.29 | 1.25 | 1.29 | 1.25 | 1.30 |
| % Conversion | 80.4 | 80.2 | 79.8  | 79.6 | 78.9 | 79.6 | 79.6 | 79.6 |
| % Selectivity| 71.5 | 70.4 | 65.5  | 64.7 | 68.0 | 67.6 | 70.5 | 70.4 |
| Wt % Yield   | 97.1 | 95.4 | 87.3  | 87.1 | 90.6 | 91.1 | 94.8 | 94.7 |

[1]1" × 5' Reactor; 3.5' bed with thermowell; 3/16" × 3/16" with 1/16" hole in center. The space velocity was 2500 h$^{-1}$
[2]Comparative

TABLE 6[1]

| Example      | 14   | 15   |
|--------------|------|------|
| Hours        | 352  | 445  |
| Salt °C.     | 376  | 386  |
| Hot Spot °C. | 434  | 448  |
| % Butane     | 1.30 | 1.30 |
| % Conversion | 79.5 | 79.8 |
| % Selectivity| 70.7 | 70.1 |
| Wt % Yield   | 95.0 | 94.5 |

[1]1" × 5' Reactor; 3.5' bed with thermowell; 3/16" × 3/16" with 1/16" hole in center. The space velocity was 2500 h$^{-1}$

TABLE 7[1]

| Example       | 16[2] | | | |
|---------------|-------|------|------|------|
| Hours         | 810   | 1858 | 2760 | 4886 |
| Salt °C.      | 388   | 394  | 398  | 398  |
| Hot Spot °C.  | 427   | 435  | 441  | 434  |
| % Butane      | 1.66  | 1.65 | 1.65 | 2.40 |
| % Conversion  | 79.5  | 80.9 | 80.6 | 80.2 |
| % Selectivity | 70.5  | 69.1 | 70.6 | 74.6 |
| Wt % Yield    | 94.7  | 94.5 | 96.2 | 101.1 |
| Example       | Comparative D[3] | | | |
| Hours         | 1007  | 1626 | 2186 | |
| Salt °C.      | 413   | 416  | 410  | |
| Hot Spot °C.  | 450   | 449  | 444  | |
| % Butane      | 1.66  | 1.64 | 1.63 | |
| % Conversion  | 79.6  | 81.2 | 81.1 | |
| % Selectivity | 68.3  | 66.2 | 65.5 | |
| Wt % Yield    | 91.9  | 90.8 | 89.8 | |

[1]1" × 12' Reactor; 10.5' bed with thermowell 3/16" × 3/16" with 1/16" hole in center. The space velocity was 2500 h$^{-1}$ except at 4886 hours in Example 16 in which the space velocity was 1800 h$^{-1}$ when tested with 2.4% butane.
[2]At life hours 810; 1858, 2760, and 4886 the corresponding % steam/TMP ppm levels were 0/0.3;0/1;1/1;2.5/2.5.
[3]At life hours 1007; 1626 and 2186 the corresponding % steam/TMP ppm levels were: 0/0;0/1;0/0.

Clear differences have been observed by XRD and SEM between the catalyst in Example 10 and the catalyst in Example 11 prepared with and without DMSO respectively. In the XRD there is observed a large difference in the ratio of the lines 3.86A°/3.14A° which was 1.15 and 0.66 for Example 10 and 11 respectively. A clear difference in morphology can be observed from the SEM analyzes for the catalyst in Example 10 prepared with DMSO and without DMSO in Example 11. This can be seen in FIGS. 3 and 4 respectively. With DMSO in the preparation, a much denser platelet layer packing with a spool shaped morphology is observed whereas for the catalyst prepared without DMSO there is observed considerably greater spacing between the platelet layers with a different shaped morphology.

The catalyst prepared in Example 10 (with DMSO) showed both higher selectivity and yield than the catalyst in Example 11 prepared without DMSO.

The catalyst in Examples 12 and 13 illustrate that the processes of preparing the catalyst can be simplified by removing the distillation step shown in both Examples 12 and 13 and with an additional further simplification in Example 13 where the rinse step was also eliminated.

In the synthesis with DMSO a foul smell of the filtered solution was noticed. To overcome this, hydrogen peroxide was added to the reaction mixture which was first cooled down and thereafter the slurry was filtered. With this additional step the good catalytic performance demonstrated with DMSO was maintained while the foul smell noticed during the filtration step was eliminated.

Example 15 illustrates a preparation procedure where the amount of benzyl alcohol was reduced while maintaining good catalytic activity.

The results in Table 7 summarize the performance of a catalyst prepared according to Example 10 which was tested in a commercial size reactor with a comparative catalyst prepared according to U.S. Pat. No. 5,364,824 (Example 7 catalyst #12). Both catalysts were prepared with the same particle size vanadium pentoxide which was mostly greater than 150 microns. The catalyst in Example 16 had higher selectivity and yield and showed lower salt bath temperature illustrating higher activity than the Comparative Example D. In addition the catalyst performed very well at high butane feed concentration of 2.4%. Thus the catalyst according to the present invention had better performance that a comparative catalyst prepared also under non corrosive conditions.

What is claimed is:

1. In a process for the preparation of a V/P/O catalyst useful for the production of maleic anhydride wherein a pentavalent vanadium compound in organic solvent solution is reduced, the improvement which comprises reducing the pentavalent vanadium compound in the presence of an organic sulfoxide having the formula:

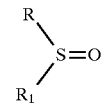

wherein R and $R_1$ are the same or different groups having 1–8 carbon atoms selected from alkyl, and aryl groups.

2. The process of claim 1 wherein the pentavalent vanadium compound is $V_2O_5$.

3. The process of claim 1 wherein the organic sulfoxide has the formula:

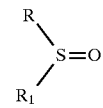

R and $R_1$ each being an alkyl group having 1–2 carbon atoms.

4. The process of claim 1 wherein the organic sulfoxide is dimethyl sulfoxide.

5. A V/P/O catalyst useful for the production of maleic anhydride prepared by the process of claim 1.

6. The catalyst of claim 5 which also comprises bismuth promoter.

* * * * *